United States Patent

Bianchi et al.

[11] Patent Number: 6,048,518
[45] Date of Patent: Apr. 11, 2000

[54] LOW RESIDUE SOLID ANTIPERSPIRANT

[75] Inventors: James Bianchi, Chicago, Ill.; Eugenia Convenido, Orlando, Fla.; Jeremy Noe, Gurnee, Ill.

[73] Assignee: Helene Curtis, Inc., Chicago, Ill.

[21] Appl. No.: 09/071,654

[22] Filed: May 1, 1998

Related U.S. Application Data

[60] Provisional application No. 60/060,114, Sep. 26, 1997.

[51] Int. Cl.⁷ .................. A61K 7/32; A61K 7/00
[52] U.S. Cl. ................. 424/65; 424/400; 424/401
[58] Field of Search ................ 424/65, 400, 401

[56] References Cited

U.S. PATENT DOCUMENTS

| | | | |
|---|---|---|---|
| 3,255,082 | 6/1966 | Barton | 424/65 |
| 3,792,068 | 2/1974 | Luedders | 424/65 |
| 4,083,956 | 4/1978 | Shelton | 424/66 |
| 4,229,432 | 10/1980 | Geria | 424/68 |
| 4,265,878 | 5/1981 | Keil | 424/68 |
| 4,425,328 | 1/1984 | Nabial | 424/68 |
| 4,724,139 | 2/1988 | Palinczar | 424/66 |
| 4,985,238 | 1/1991 | Tanner et al. | 424/66 |
| 5,292,530 | 3/1994 | McCrea et al. | 424/66 |
| 5,433,943 | 7/1995 | Osipow et al. | 424/65 |
| 5,486,347 | 1/1996 | Callaghan et al. | 423/623 |

FOREIGN PATENT DOCUMENTS

| | | |
|---|---|---|
| 028853 | 5/1981 | European Pat. Off. . |
| 0135315 | 3/1985 | European Pat. Off. . |
| 0295070 | 12/1988 | European Pat. Off. . |
| 0388110 | 9/1990 | European Pat. Off. . |
| 0388111 | 9/1990 | European Pat. Off. . |
| 97/15270 | 5/1997 | WIPO . |
| 97/16162 | 5/1997 | WIPO . |
| 98/24404 | 6/1998 | WIPO . |

OTHER PUBLICATIONS

International Search Report Application No. PCT/EP 98/05497 mailed Apr. 16,1999.

*Primary Examiner*—Shelley A. Dodson
*Attorney, Agent, or Firm*—Matthew Boxer

[57] ABSTRACT

The present invention is directed to a low residue antiperspirant composition substantially free of water and long chain fatty alcohols which comprises:

(a) from about 30% to about 50% of a volatile silicone;

(b) from about 5% to about 30% of a particulate antiperspirant active;

(c) from about 2% to about 12% of hydrogenated castor oil;

(d) from about 8% to about 28% of paraffin; and (e) from about 10% to about 25% of an emollient;

wherein the ratio of the paraffin to hydrogenated castor oil is from about 6 to 1 to about 0.85 to 1.

9 Claims, No Drawings

LOW RESIDUE SOLID ANTIPERSPIRANT

Under 35 USC §119(e), this application claims the benefit of prior provisional application, Ser. No. 60/060,114, filed Sept. 26, 1997.

FIELD OF THE INVENTION

The present invention relates to antiperspirant sticks, substantially free of water and long chain fatty alcohols, which provide the user with excellent antiperspirant efficacy, reduced residue when the composition is first applied to the skin, reduced residue after dry down, high temperature stability, and excellent cosmetics and aesthetics.

BACKGROUND OF THE INVENTION

Many solid antiperspirants have been described in the chemical and cosmetic literature. These compositions generally tend to fall into one of two classes: emulsion sticks and suspensoid sticks. Emulsion sticks contain a solution of the antiperspirant active incorporated in the stick via an emulsion. Although emulsion sticks may be desirable in certain respects, they tend to be unstable, have poor aesthetics and leave a visible residue on the skin after use. Suspensoid sticks contain the powdered antiperspirant active suspended in the stick without the use of water or an emulsion. While suspensoids tend to be stable, they may be brittle and hard and more importantly, they tend to leave an unsightly white residue chalky residue after application. This residue is not only aesthetically displeasing to the user, but can also soil clothing. The present invention provides an excellent antiperspirant composition which does not leave a chalky white residue upon application. The excellent antiperspirant compositions of the invention are often in the form of suspensoid sticks.

Patents and patent documents related to this field of invention are as follows:

| | |
|---|---|
| USP 3,255,082; | Barton et al; |
| USP 3,986,203; | Spitzer et al;. |
| USP 4,083,956 | Shelton; |
| EPA 28,853 | Beckmeyer et al; |
| USP 4,425,328, | Nabial et al; |
| USP 4,265,878, | Keil; |
| USP 4,229,432, | Geria; |
| USP 4,724,139, | Palinczar |
| USP 4,985,238 | Tanner en and |
| USP 5,486,347, | Callaghan et al. |

SUMMARY OF THE INVENTION

The present invention is directed to a low residue antiperspirant composition substantially free of water and long chain fatty alcohols which comprises:

(a) from about 30% to about 50% of a volatile silicone;

(b) from about 5% to about 30% of a particulate antiperspirant active;

(c) from about 20% to about 12% of hydrogenated castor oil:

(d) from about 8% to about 28% of paraffin; and (e) from about 10% to about 25% of an emollient;

wherein the ratio of the paraffin to hydrogenated castor oil is from about 6 to 1 to about 0.85 to 1.

The present invention is also directed to a method for preventing and controlling perspiration wetness in humans comprising the application to the underarm area of an effective amount of the composition as above.

DETAILED DESCRIPTION OF THE INVENTION

As used herein % means weight %, unless otherwise specified.

All of the ingredients used to prepare the compositions of the invention are known.

The present invention is directed to a low residue antiperspirant composition substantially free of water and long chain fatty alcohols which comprises:

(a) from about 30% to about 50% of a volatile silicone;

(b) from about 5% to about 30% of a particulate antiperspirant active;

(c) from about 2% to about 12% of hydrogenated castor oil;

(d) from about 8% to about 28% of paraffin; and (e) from about 10% to about 25% of an emollient;

wherein the ratio of the paraffin to hydrogenated castor oil is from about 6 to 1 to about 0.85 to 1.

The present invention is also directed to a composition as above wherein the ratio of paraffin to hydrogenated castor oil to is from about 4 to 1 to about 1 to 1.

The present invention is also directed to a composition as above wherein the ratio of paraffin to hydrogenated castor oil to is from about 2.5 to 1 to about 1 to 1.

The present invention is also directed to a composition as above wherein the volatile silicon is present in a range of about 35% to about 45%.

The present invention is also directed to a composition as above wherein the particulate antiperspirant active is present in a range of about 20% to about 25%.

The present invention is also directed to a method for preventing and controlling perspiration wetness in humans comprising the application to the underarm area of an effective amount of the composition as above.

The present invention is also directed to process for preparing antiperspirant compositions of the invention.

Paraffinic Hydrocarbon

The branched chain hydrocarbons useful in the present invention are branched non-volatile aliphatic waxes.

Paraffin is a solid mixture of hydrocarbons obtained from petroleum characterized by relatively large crystals.

The preferred branched hydrocarbon used in the compositions of the invention is paraffin.

A paraffin material which can be used in the present invention is available under the tradename "Paraffin Wax S.P. 173" sold by Strahl & Pitsch, Inc.

P.O. Box 1098

West Babylon, N.Y. 11704

(516) 587-9000

Specifications:

Melting Point—USP Class II—Open capillary tube 136–142 F Penetration—ASTM D-1321 @ 100/77/5 10–16.

Antiperspirant Material

The present compositions contain from about 5% to about 30% by weight of a particulate antiperspirant material. These weight percentages are calculated on an anhydrous metal salt basis (exclusive of glycine, the salts of glycine, or other complexing agents). The particulate antiperspirant material preferably has particle sizes ranging from about 1 to about 100 microns, more preferably from about 1 to about 50 microns. They may be in impalpable or microscopic in form and preferably have a high bulk density (e.g. greater than about 0.7 g/cm³). Such materials include, for example, many aluminum or zirconium astringent salts or complexes and are well known in the art.

Any aluminum astringent antiperspirant salt or aluminum and/or zirconium astringent complex in particulate form can be employed herein. Salts useful as astringent antiperspirant salts or as components of astringent complexes include aluminum halides, aluminum hydroxyhalides, zirconyl oxy halides, zirconyl hydroxyhalides and mixtures of these salt materials.

Aluminum salts of this type include aluminum chloride and the aluminum hydroxy halides having the general formula $Al_2(OH)_xQ_yXH_2O$ where Q is chlorine, bromine, or iodine; x is from about 2 to about 5, and x+y is about 6 and x and y do not need to be integers and where X is from about 1 to about 6. Aluminum salts of this type can be prepared in the manner described more fully in U.S. Pat. No. 3,887,692 to Gilman, U.S. Pat. No. 3,904,741 Jones and Rubino, both of which are herein incorporated by reference.

The zirconium salts which are useful in the present invention include both zirconium oxy salts and zirconium hydroxyl salts, also referred to as zirconyl hydroxy salts. These compounds may be represented by the following general empirical formula:

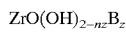

$$ZrO(OH)_{2-nz}B_z$$

wherein z may vary from about 0.9 to about 2 and need not be an integer, n is the valence of B, 2–nz is greater than or equal to 0. and B may be selected from the group consisting of halides, nitrate, sulfamate, sulfate, and mixtures thereof. Although only zirconium and aluminum compounds are exemplified in the specification, it will be understood that other metals such as the Group IV B metals, including hafnium could be used in the present invention.

As with the basic aluminum compounds. It will be understood that the above formula is greatly simplified and is intended to represent and include compounds having coordinated and/or bound water in various quantities as well as polymers, mixtures and complexes of the above. As will be seen from the above formula the zirconium hydroxy salts actually represent a range of compounds having various amounts of the hydroxy group, varying from about 1.1 to only slightly greater than 0 groups per molecule.

Several types of antiperspirant complexes using the above antiperspirant salts are known in the art. For example, U.S. Pat. No. 3,792,068 Luedders et al., herein incorporated by reference, discloses complexes of aluminum, zirconium and amino acids such as glycines. Complexes such as those disclosed in Luedders and other similar complexes are commonly known as ZAG(OR Zag). ZAG complexes are chemically analyzable for the presence of aluminum, activated ZAG compounds and chlorine. ZAG complexes useful herein are identified by the specification of both the molar ratio of aluminum to zirconium (the Al:Zr ratio) and the molar ratio of total metal to chlorine (metal:Cl) ZAG complexes useful herein have an Al:Zr ratio of from about 1.67 to about 12.5 and a metal:Cl ratio of about 0.73 to about 1.93.

Another patent which discloses ZAG compounds is U.S. Pat. No. 4,985,238 to Tanner et al. This just-mentioned patent is herein incorporated by reference. Preferred ZAG complexes are described in U.S. Pat. No. 4,985,238 to Tanner et al.

Another patent which discloses activated ZAG compounds (AZAG or AZG compounds) is U.S. Pat. No. 5,486,347 to Callaghan et al. This just-mentioned patent is herein incorporated by reference. Activated ZAG compounds may be employed as the particulate antiperspirant active in the compositions of the present invention.

Activated ZAG compounds may be prepared by heating an aqueous solution containing an aluminum chlorhydroxide component and mixing it with a zirconium hydroxy chloride component.

Volatile Silicone

Volatile silicones are known for use in deodorant sticks. The volatile silicone component is preferably either a cyclic or a linear polydimethylsiloxane and is present at a level of from about 30 to about 50%, preferably from about 35% to about 45%. The volatile silicones are more fully described in U.S. Pat. No. 4,985,238 which is herein incorporated by reference.

Hydrogenated Castor Oil

Hydrogenate castor oil is the end product of the controlled hydrogenation of castor oil and is described on page 315 of the International Cosmetic Ingredient Dictionary 5th ed., 1993, which is hereby incorporated by reference.

Emollient

Emollients suitable for use in the compositions of the present invention are known in the art and include a nonvolatile silicone oil, a high molecular weight polypol, an oil-surfactant, an aromatic ester, an aliphatic ester, and similar organic compounds.

Optional Ingredients

In addition to the ingredients listed above, the anhydrous, topically-effective compositions of the present invention also can include other optional ingredients that are conventionally included in topical cosmetic and medicinal compositions. For example, fragrances can be incorporated into the anhydrous, topically-effective composition in an amount of from 0% to about 5% based on the total weight of the composition. The composition of the present invention, when applied to skin, therefore fixes a substantive fragrance film on the skin that resists moisture, but that can be removed by washing. Other optional ingredients that can be included in the anhydrous composition of the present invention include, but are not limited to, drying agents, like talc or DRY FLO (aluminum starch octenylsuccinate); preservatives; and dyes. Generally, such optional ingredients are present in a composition of the present invention in an amount of about 10% or less by weight. In addition, although the necessity of including an organoclay is virtually eliminated by the use of the new and improved suspending agent, an organoclay can be included in a composition of the present invention as an additional suspending agent in an amount of up to 20% by weight of the composition. An organoclay is especially helpful as an anticaking agent to maintain a particulate topically-effective compound homogeneously dispersed throughout the composition. An exemplary organoclay is a quaternized three-layer clay exfoliated with a polar solvent, like a quaternized montmorillonite clay exfoliated with propylene carbonate.

The compositions of the invention are prepared by combining all of the ingredients except the antiperspirant active, the fragrance (if present), and the talc (if present). The resulting mixture is heated with stirring at a temperature of from about 165 F to about 185 F, until all of the waxes are completely melted or until all particulates are well-dispersed. The antiperspirant active, and the talc (if present) are added to the molten wax at any temperature between about 165 F to about 185 F. The fragrance (if present) is added at about 165 F. The mixture is then filled into cannisters at 165 F, or it is cooled to a temperature in the range of about 145 F to about 165 F, and then filled into cannisters. It is preferred to fill the cannisters when the mixture is at 165 F. In the cannisters, the compositions further cool to room temperature and harden.

The following specific examples are illustrative of the anhydrous, topically-effective compositions of the present invention. However, it should be understood that the present invention is not limited to the specific examples set forth below. In the following examples, all amounts of the various ingredients are expressed by weight percentages unless otherwise specified.

EXAMPLES A, B, C, D, E, F, G, AND H

| Ingredient | A | B | C | D | E | F | G | H |
|---|---|---|---|---|---|---|---|---|
| Cyclomethicone DC245 | 40.3 | 38.0 | 37 | 41.32 | 41.57 | 36.49 | 39 | 36 |
| Phenyl Trimethicone DC556 | | | 4 | | | 2.0 | | 2 |
| Paraffin wax | 16.92 | 9.25 | 18 | 16.05 | 16.05 | 9.37 | 17 | 12.08 |
| SF1642 Silicone wax | | 7.75 | | 1 | | 3.22 | | |
| Castorwax | 6.85 | 10.0 | 3 | 5.98 | 5.98 | 10.13 | 7 | 10.98 |
| PEG-8 Distearate | 2.85 | | | 4.5 | 4.2 | 4.63 | | 4.94 |
| Hydrogenated Vegetable oil | | | | | | | 1 | |
| Finsolv TN | 1.55 | | | | 1 | | 2 | |
| PPG-14 Butyl ether | 10.03 | 12.5 | 12.5 | 10.4 | 10.4 | 12.66 | 10 | 12.5 |
| AZG-370 | 20.00 | 22.0 | 22.0 | 20.0 | 20 | 20 | 22 | 20 |
| Talc | | | 1.5 | | | | | |
| Fragrance | 1.50 | 0.5 | 2.0 | 0.75 | 0.8 | 1.5 | 2 | 1.5 |

The numbers in the above table are weight %'s.

EXAMPLES I, J, K, L, M, N, O, P, Q AND R

The ingredients in the tables below are in weight %'s.

| Ingredient | I | J | K | L | M | N |
|---|---|---|---|---|---|---|
| Cyclomethicone DC245 | 41.05 | 41.32 | 38.85 | 36.8 | 39.10 | 37.07 |
| Paraffin wax | 16.92 | 16.05 | 16.01 | 16.92 | 15.19 | 16.05 |
| Castorwax | 6.85 | 5.98 | 6.48 | 6.85 | 5.66 | 5.98 |
| PPG-14 Butyl ether | 10.03 | 10.40 | 9.49 | 10.03 | 9.84 | 10.40 |
| Finsolv TN | 1.55 | — | 1.47 | 1.55 | — | — |
| PEG-8 Distearate | 2.85 | 4.50 | 2.70 | 2.85 | 4.26 | 4.50 |
| SF 1642 | — | 1.00 | — | — | 0.95 | 1.00 |
| AZG-370 | 20.00 | 20.0 | — | — | — | — |
| Q 5-7167 | — | — | 24.00 | 24.00 | 24.00 | 24.00 |
| Fragrance | 0.75 | 0.75 | 1.00 | 1.00 | 1.00 | 1.00 |

| Ingredient | O | P | Q | R |
|---|---|---|---|---|
| DC 345 | 38.85 | 36.80 | 39.10 | 37.07 |
| Paraffin wax | 16.01 | 16.92 | 15.19 | 16.05 |
| Castorwax | 6.48 | 6.85 | 5.66 | 5.98 |
| Fluid AP | 9.49 | 10.03 | 9.84 | 10.40 |
| Finsolv TN | 1.47 | 1.55 | — | — |
| Estol EO4DS3724 | 2.70 | 2.85 | 4.26 | 4.50 |
| SF 1642 | — | — | 0.95 | 1.00 |
| AZG-370 | — | — | — | — |
| Q 5-7167 | 12.00 | 12.00 | 12.00 | 12.00 |
| AZG 6313-15 | 12.00 | 12.00 | 12.00 | 12.00 |
| Fragrance | 1.00 | 1.00 | 1.00 | 1.00 |

| Ingredient | S | T | U |
|---|---|---|---|
| CYCLOMETHICONE DC 245 | 34.8 | 37.8 | 36.7 |
| PHENYL TRIMETHICONE DC556 | — | — | — |
| Paraffin wax | 8.5 | 9.25 | 9.05 |
| SF 1642 Silicone Wax | 1.5 | 1.5 | 1 |
| Castor wax | 10.5 | 6.85 | 8 |
| PEG-8 Distearate | 5.5 | 9.25 | 5 |
| Hydrogenated Vegetable Oil | — | — | — |
| Finsolv TN | — | — | — |
| PPG-14 Butyl Ether | 18.5 | 16 | 16.5 |
| AZG-370 | 20 | 20 | — |
| W ZR3OB DM CP5** | — | — | 23 |
| Talc | — | — | — |
| Fragrance | 0.7 | 0.7 | 0.75 |

**Aluminum Zirconium Trichlorohydrex-Gly

The compositions of the present invention are excellent antiperspirant compositions which do not leave a chalky white residue upon application. This can be demonstrated by applying compositions of the present invention to a dark substrate and instrumentally measuring the intensity of any whiteness that results.

One important physical parameter affecting consumer acceptance of suspensoid antiperspirant sticks of the invention is hardness as measured by needle penetration. Typical compositions of the invention will range in hardness from about 7.0 to about 14.0 mm as shown by the above mentioned needle penetration test. Products outside this range will typically generate low consumer acceptance ratings.

The following experimental results demonstrate the properties of the claimed compositions.

Summary of Experimental Methods

An in vitro method was used to quantify the relative amount of whitening of two antiperspirant sticks. The formulas of these two sticks are shown below.

At 95% confidence, the instrumental lightness measurements using a chromometer show the Composition 1 residue to be significantly whiter than that of Composition 2 one minute after application on gray sandpaper. After two hours drying at room temperature, the residue from Composition 1 is whiter than after application, while the Composition 2 residue is less white than after application and is not significantly different from the sandpaper. Visual observation of the treated sandpaper indicates that Composition 1 is very clear, while the Composition 2 residue is very white.

Method

The surface of the sticks were cut with a knife to yield a flat surface for application. The sticks were applied by hand, using an even pressure, onto gray 1200 grit sandpaper (Grainger). Each application consisted of 4 strokes covering an area of 2.5×20 cm (50 cm$^2$). Three duplicate applications of each product were made.

The Minolta Chromameter was set to read in the L*a*b* measuring mode and was used to measure the color of the residue from the formulation on the sandpaper. One minute after application, the L* value, a measure of the lightness (whiteness), was acquired on five sites in each application area. The most uniform areas were used for the measuring sites and either end was avoided because of the stick "footprint" present. Thus, fifteen measurements were obtained for each formulation one minute after application.

The stick residue on the sandpaper was allowed to dry for two hours at room temperature. The L* value was again acquired on the five sites in each application area, yielding fifteen measurements for each formulation.

Differences between the two formulations and the sandpaper at these two time points were determined using analysis of variance followed by a post-hoc Scheffe test at p<0.05.

| Scheffe Test; Variable: L* - 1 minute after application of products | | | |
|---|---|---|---|
| Product | Composition 1 mean = 49.93 | Composition 2 mean = 45.33 | Sandpaper mean = 42.02 |
| Composition 1 | — | .000000** | .000000** |
| Composition 2 | .000000** | — | .000000** |
| Sandpaper | .000000** | .000000** | — |

**Marked differences are significant at p < .05000

| Scheffe Test; Variable: L* - 2 hours after application of products | | | |
|---|---|---|---|
| Product | Composition 1 mean = 65.23 | Composition 2 mean = 41.55 | Sandpaper mean = 42.02 |
| Composition 1 | — | .000000** | .000000** |
| Composition 2 | .000000** | — | .771653 |
| Sandpaper | .000000** | .771653 | — |

**Marked differences are significant at p < .05000

Conclusions

A higher L* value indicates a lighter (whiter) formulation on the sandpaper substrate.

One minute after application:

Results indicate that the residue from Composition 1 is less white than that of Composition 2. The results of the Scheffe test show that this difference is significant at the 95% confidence level. This statistical analysis, at the 95% confidence level, shows that the composition 2 residue is whiter than the sandpaper at this one minute time point.

Two hours after application:

The residue from Composition 1 is less white that that of Composition 2. The Composition 2 residue is much whiter after drying than it was 1 minute after application, and the results of the Scheffe test, at the 95% confidence level, show that this residue is not significantly different in whiteness from the sandpaper at this 2 hour time point.

Visual observations of the sandpaper after drying for two hours:

The residue from Composition 2 on the sandpaper is extremely white, while that from Composition 1 is colorless.

| Stearyl Alcohol Composition: 2 | | Non-Stearyl Alcohol Compositions: 1 | |
|---|---|---|---|
| | Wt.% | | Wt.% |
| Cyclomethicone | 46.00 | Cyclcmethicone | 41.32 |
| Stearyl Alcohol | 15.00 | Pararfin Wax | 16.05 |
| Castor Wax | 3.00 | Castor Wax | 5.98 |
| Hydrogenated Vegetable Oil | 1.50 | PEG-8 Distearate | 4.50 |
| Octyl Isononanoate | 6.00 | PEG-14 Butyl Ether | 10.40 |
| Glyceryl Stearate & PEG-100 Stearate | 1.00 | Silicone Wax 1642 | 1.00 |
| Talc | 3.50 | AZG-370 | 20.0 |
| AZG 370 | 22.00 | Fragrance | 0.75 |
| Fragrance | 2.00 | | |

In a similar manner the following Compositions, 3 and 4 were tested for relative amount of whitening.

Results

| Scheffe Test: Variable: L*VALUE - After product has dried on the sandpaper Homogeneous Groups, p < 0.05 | | | |
|---|---|---|---|
| | Sandpaper | 3 | 4 |
| Sandpaper | 42.02 | xxxx | |
| Composition 3 | 42.42 | xxxx | |
| Composition 4 | 55.86 | | xxxx |

The results of the Scheffe test indicate that, at the 95% confidence level, there is no significant difference of whiteness between the residue from Composition 3 and sandpaper with no product applied. The residue from Composition 4, containing stearyl alcohol is significantly whiter than the residue of Composition 3 and also the sandpaper.

Conclusions

A higher L* value indicates a whiter formulation residue on the sandpaper s substrate.

After drying at room temperature, the residue from Composition 4 is significantly whiter than the residue from Composition 3. The statistical analysis of the results also shows that, at the 95% confidence level, the residue from Composition 3 is not significantly different in whiteness from the untreated sandpaper.

Compositions 3 and 4 are as follows:

| Composition | Composition 3 | Composition 4 |
|---|---|---|
| Cyclomethicone | 41.32 | 41.32 |
| Stearyl Alcohol | | 22.03 |
| Paraffin Wax | 16.05 | |
| Castor Wax | 5.98 | |
| PEG-8 Distearate | 4.50 | 4.50 |
| SF-1642 Wax | 1.50 | 1.50 |
| PPG-14 Butyl Ether | 10.40 | 10.40 |
| AZG-370 | 20.00 | 20.00 |

What is claimed is:

1. A low residue antiperspirant composition substantially free of water and long chain fatty alcohols which comprises:
   (a) from about 30% to about 50% of a volatile silicone;
   (b) from about 5% to about 30% of a particulate antiperspirant active;
   (c) from about 2% to about 12% of hydrogenated castor oil;
   (d) from about 8% to about 28% of paraffin; and
   (e) from about 10% to about 25% of an emollient;
   wherein the ratio of the paraffin to hydrogenated castor oil is from about 6 to 1 to about 0.85 to 1.

2. A composition according to claim 1, wherein the ratio of paraffin to hydrogenated castor oil to is from about 4 to 1 to about 1 to 1.

3. A composition according to claim 1, wherein the ratio of paraffin to hydrogenated castor oil to is from about 2.5 to 1 to about 1 to 1.

4. A composition according to claim 1, wherein the volatile silicon is present in a range of about 35%, to about 45%.

5. A composition according to claim 1, wherein the particulate antiperspirant active is present in a range of about 20% to about 25%.

6. A method for preventing and controlling perspiration wetness in humans comprising the application to the underarm area of an effective amount of the composition according to claim 1.

7. A process for preparing a composition of claim 1 which comprises:
(1) combining:
   (a) a volatile silicone;
   (b) hydrogenated castor oil;
   (c) paraffin; and
   (d) an emollient;
   wherein the ratio of the paraffin to hydrogenated castor oil is from about 6 to 1 to about 1 to 1;
(2) the resulting mixture is heated with stirring at a temperature of from about 165 F to about 185 F, until all of the waxes are completely melted or until all particulates are well-dispersed:
(3) adding an antiperspirant active, and
(4) filling the mixture into a canister at 165F; or cooling the mixture to a temperature in the range of about 145 F to about 165 F, filling the mixture into a canister; and
(5) allowing the mixture to cool to room temperature and harden.

8. A process according to claim 7 wherein the mixture in step 4 is filled into a canister when the mixture is at about 165 F.

9. A process according to claim 7 wherein in step 3, the antiperspirant active is filled at 185 F, and wherein in step 3, talc is further added at 185 F.

* * * * *